United States Patent [19]

Narula et al.

[11] Patent Number: 5,665,698
[45] Date of Patent: Sep. 9, 1997

[54] METHYL SUBSTITUTED TETRAHYDROINDANE ALKYL ENOL ETHERS, PERFUMERY USES THEREOF, PROCESSES FOR PREPARING SAME, AND PROCESS INTERMEDIATES

[75] Inventors: Anubhav P. S. Narula; James Joseph Koestler, both of Hazlet, N.J.; Peter J. Hartong, AN Naarden, Netherlands; Marie R. Hanna, Keyport; Charles E. J. Beck, Summit, both of N.J.

[73] Assignee: International Flavors & Fragrances Inc., New York, N.Y.

[21] Appl. No.: 709,506

[22] Filed: Sep. 6, 1996

[51] Int. Cl.$^6$ ............................................ A61K 7/46
[52] U.S. Cl. ............... 512/19; 568/591; 568/665
[58] Field of Search ............... 512/19; 568/591, 568/665

[56] References Cited

U.S. PATENT DOCUMENTS

| | | | |
|---|---|---|---|
| 3,636,165 | 1/1972 | Hall | 512/19 |
| 4,902,672 | 2/1990 | Sprecker et al. | 512/19 |
| 4,959,349 | 9/1990 | Ohnuma et al. | 568/665 |
| 5,403,823 | 4/1995 | Frank | 512/17 |

*Primary Examiner*—James H. Reamer
*Attorney, Agent, or Firm*—Arthur L. Liberman

[57] ABSTRACT

Described are methyl substituted tetrahydroindane alkyl enol ethers defined according to the structure:

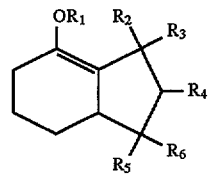

wherein $R_1$ represents methyl or ethyl; wherein $R_4$ represents methyl or hydrogen; wherein $R_2$, $R_3$, $R_5$ and $R_6$ each represents methyl or ethyl with the provisos that:

(1) at least three of $R_2$, $R_3$, $R_5$ and $R_6$ represent methyl; and (2) when each of $R_2$, $R_3$, $R_5$ and $R_6$ is methyl, then $R_4$ is methyl and uses thereof in augmenting, enhancing or imparting an aroma in or to perfume compositions, colognes and perfumed articles including but not limited to perfumed polymers, solid or liquid anionic, cationic, nonionic or zwitterionic detergents, fabric softener compositions, fabric softener articles, cosmetic powders and hair preparations. Also described are processes for preparing same as well as the process intermediates defined according to the structure:

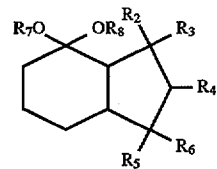

wherein $R_7$ and $R_8$ are the same or different methyl or ethyl and wherein $R_2$, $R_3$, $R_4$, $R_5$ and $R_6$ are defined, supra.

11 Claims, 11 Drawing Sheets

FIG.I
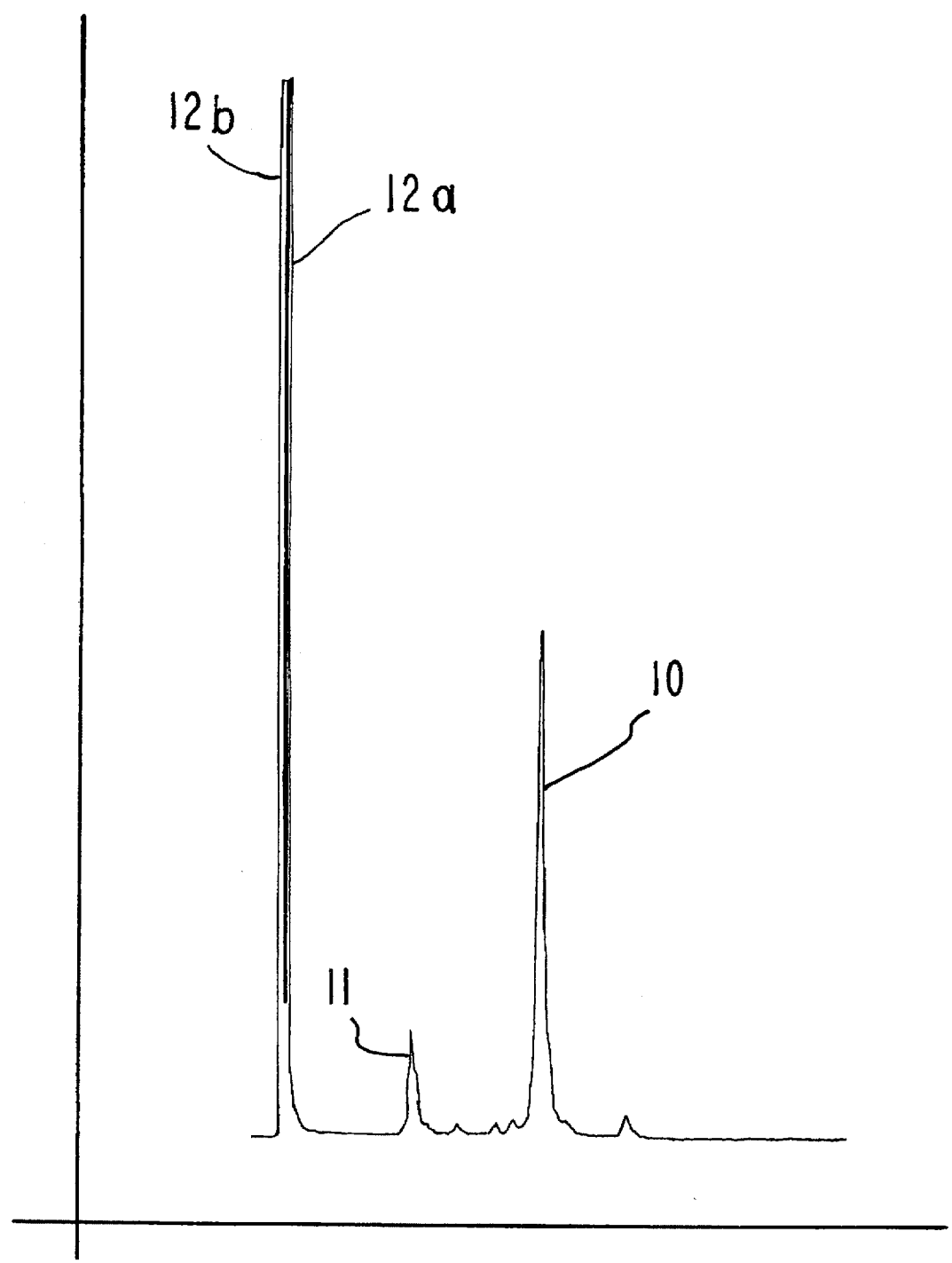
GLC PROFILE FOR EXAMPLE I.

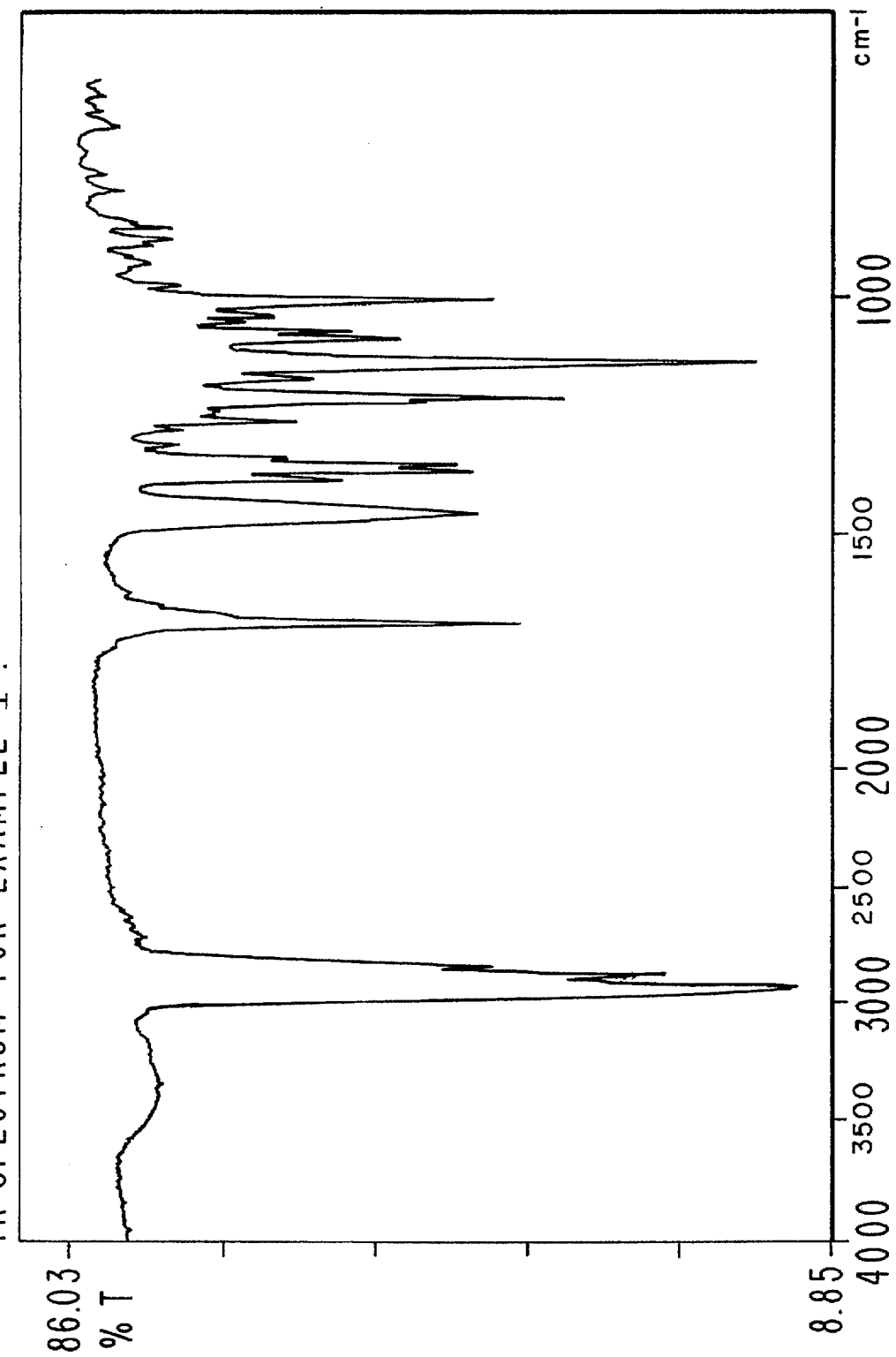

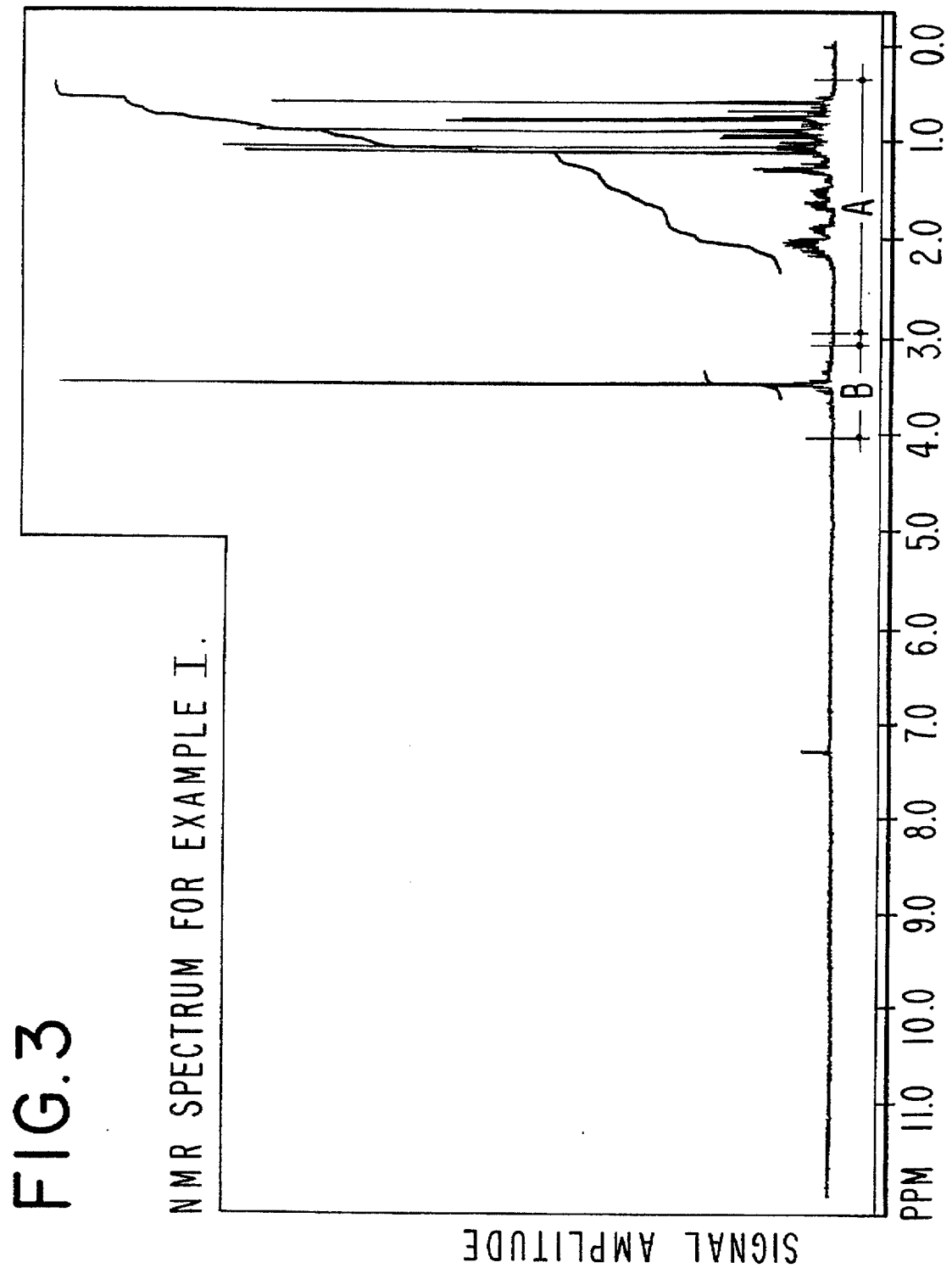

GLC PROFILE FOR EXAMPLE II.

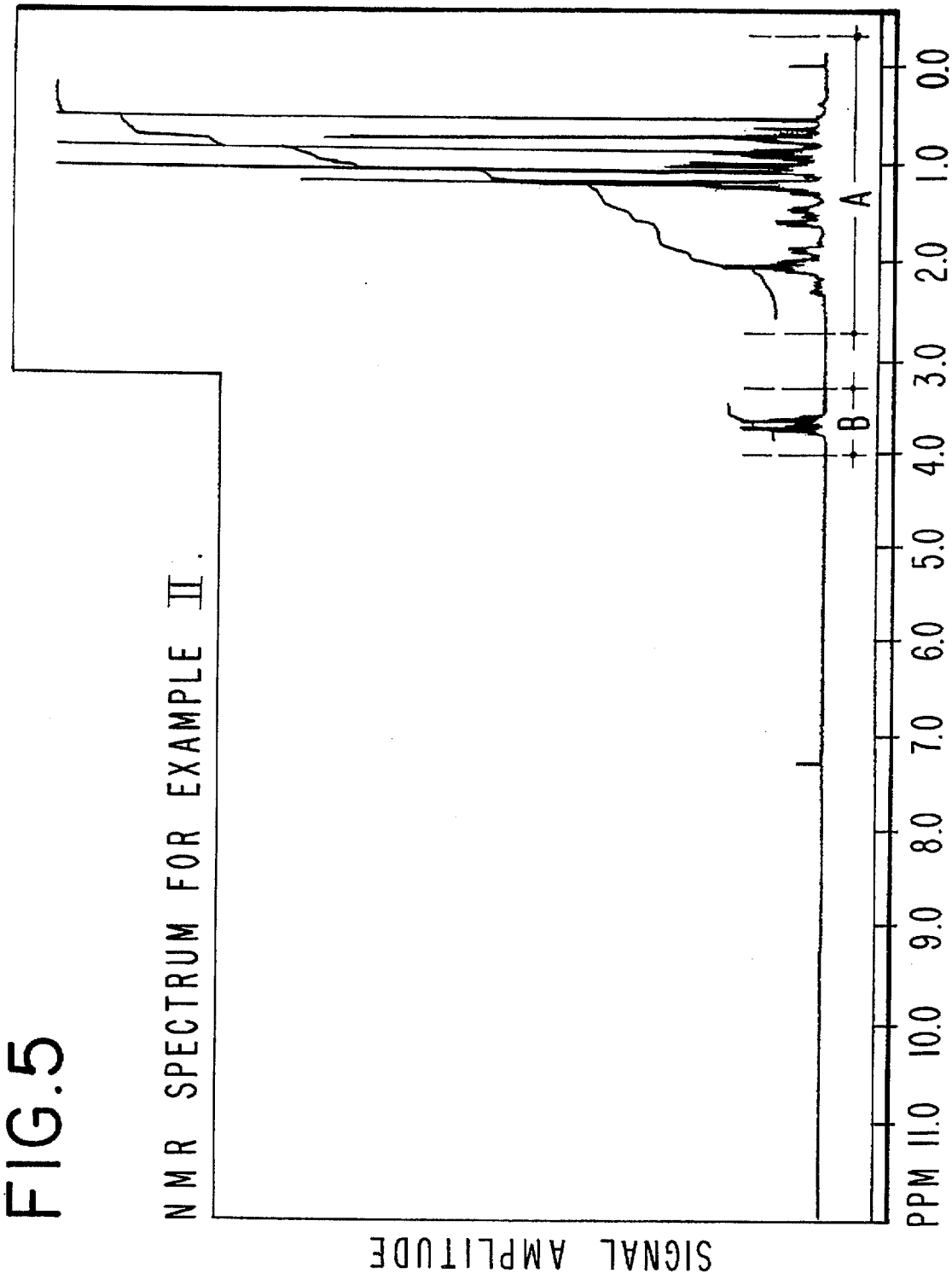
FIG.5 NMR SPECTRUM FOR EXAMPLE II.

IR SPECTRUM FOR EXAMPLE II.

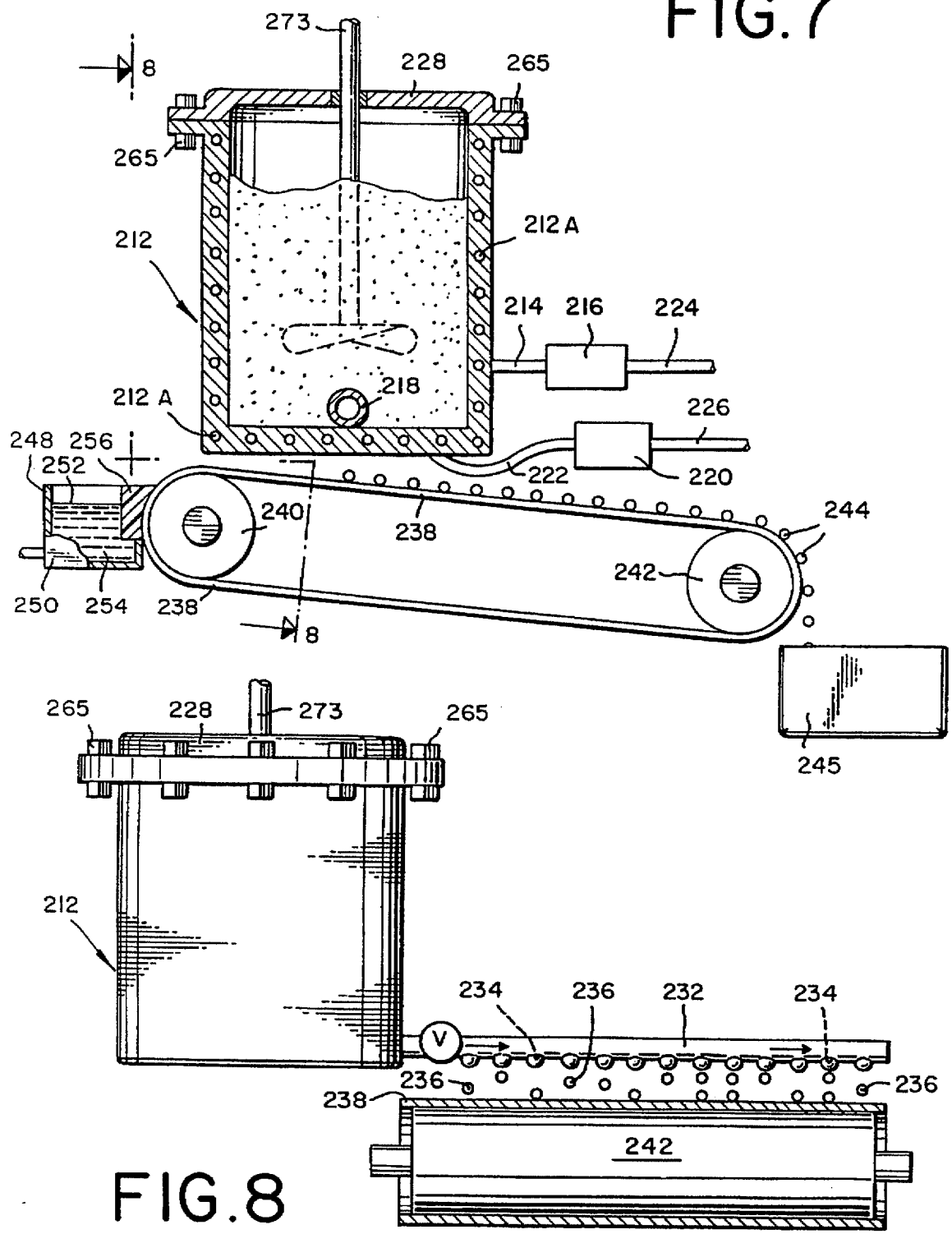

5,665,698

METHYL SUBSTITUTED TETRAHYDROINDANE ALKYL ENOL ETHERS, PERFUMERY USES THEREOF, PROCESSES FOR PREPARING SAME, AND PROCESS INTERMEDIATES

BACKGROUND OF THE INVENTION

This invention relates to methyl substituted tetrahydroindane alkyl enol ethers having the generic structure:

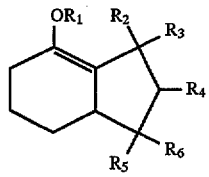

wherein $R_1$ represents methyl or ethyl; wherein $R_4$ represents methyl or hydrogen; wherein $R_2$, $R_3$, $R_5$ and $R_6$ each represents methyl or ethyl with the provisos that:

(1) at least three of $R_2$, $R_3$, $R_5$ and $R_6$ represent methyl; and (2) when each of $R_2$, $R_3$, $R_5$ and $R_6$ is methyl, then $R_4$ is methyl and uses thereof in augmenting, enhancing or imparting an aroma in or to perfume compositions, colognes and perfumed articles.

Materials which can provide sweet, musky, woody, balsamic and amber aromas with woody, balsamic, amber, powdery, sweet and musky topnotes are highly desirable in the art of perfumery. Many of the natural substances which provide such fragrance nuances and contribute the desired nuances to perfumery compositions are high in cost, vary in quality from one batch to another and/or are generally subject to the usual variations of natural products.

The prior art contains teachings regarding the use of alkyl ethers of tetrahydro substituted methyl indane derivatives defined according to the structures:

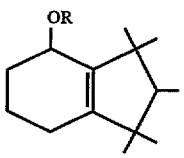

wherein R is alkyl such as methyl and:

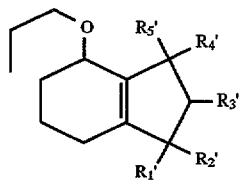

wherein $R_3'$ represents methyl or hydrogen; and wherein $R_1'$, $R_2'$, $R_4'$ and $R_5'$ each represents methyl or ethyl with the provisos that:

(1) at least three of $R_1'$, $R_2'$, $R_4'$ and $R_5'$ is methyl; and (2) when each of $R_1'$, $R_2'$, $R_4'$ and $R_5'$ is methyl, then $R_3'$ is methyl.

Thus, U.S. Pat. No. 3,636,165 (Hall) discloses the genus defined according to the structure:

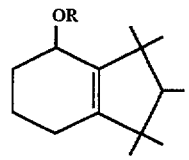

including the compound having the structure:

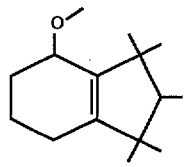

for their perfume uses. Hall indicates that the compound having the structure:

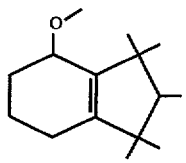

has a balsamic, woody aroma. Sprecker, et al discloses the perfumery uses of a mixture of compounds defined according to the structure:

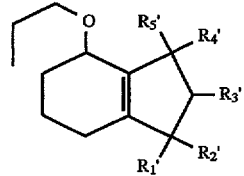

wherein the mixture of such compounds has a musky, cigar box-like, amber, woody, patchoulie and camphoraceous aroma with woody and winey topnotes.

However, the methyl substituted tetrahydroindane alkyl enol ethers of our invention have structural differences which are different in kind rather than degree from the structures of the ethers of the prior art. Furthermore, the substantivities and strengths of the methyl substituted tetrahydroindane alkyl enol ethers of our invention are unexpectedly, unobviously and advantageously different from the ethers of the prior art including those disclosed in U.S. Pat. Nos. 3,636,165 and 4,902,672.

BRIEF DESCRIPTION OF THE DRAWINGS

FIG. 1 is the GLC profile for the reaction product of Example I containing a mixture of compounds defined according to the structure:

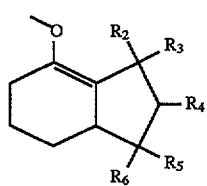

which mixture includes the compounds having the structures:

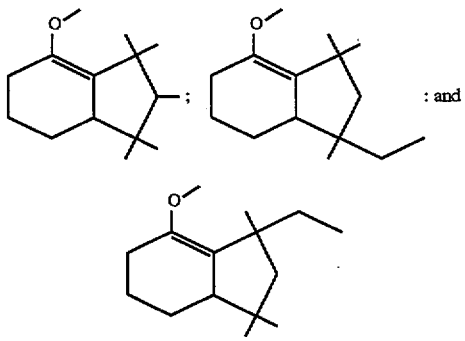

(conditions: SE-30 column programmed at 100°–220° C. at 8° C. per minute).

FIG. 2 is the infrared spectrum for the mixture of compounds having the structures:

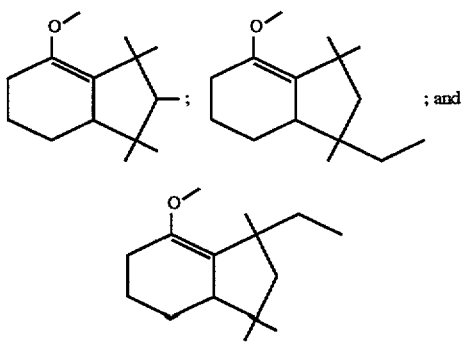

prepared according to Example I.

FIG. 3 is the NMR spectrum for the mixture of compounds having the structures:

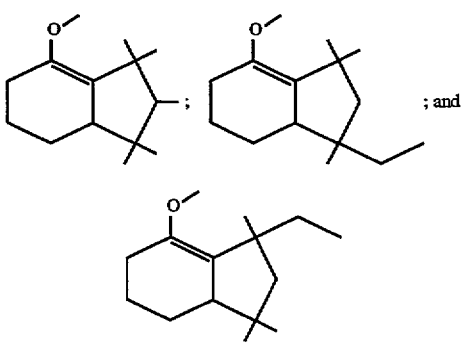

prepared according to Example I.

Figure 3A:
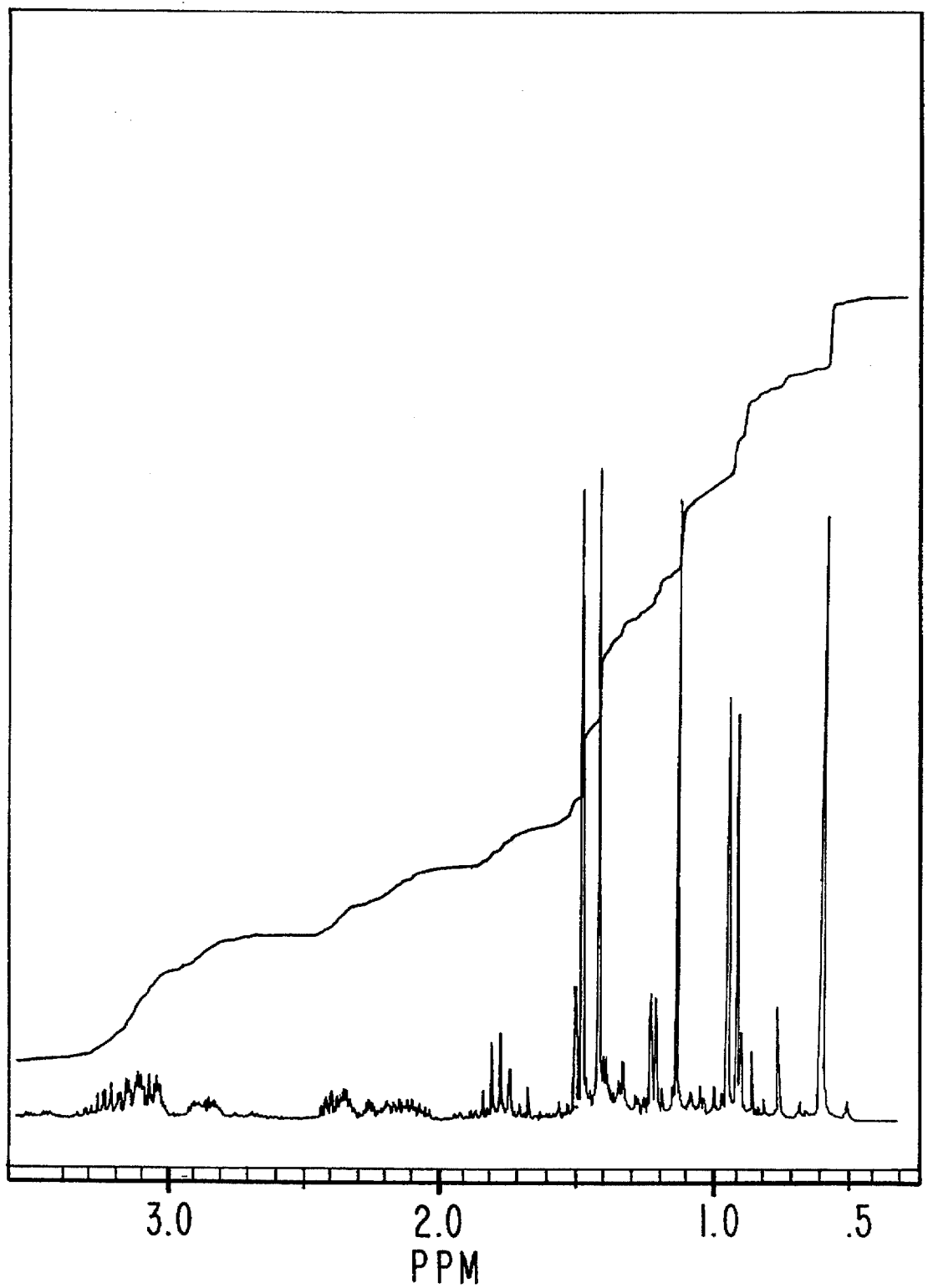

FIG. 3A is an enlargement of section "A" of the NMR spectrum of FIG. 3.

Figure 3B:
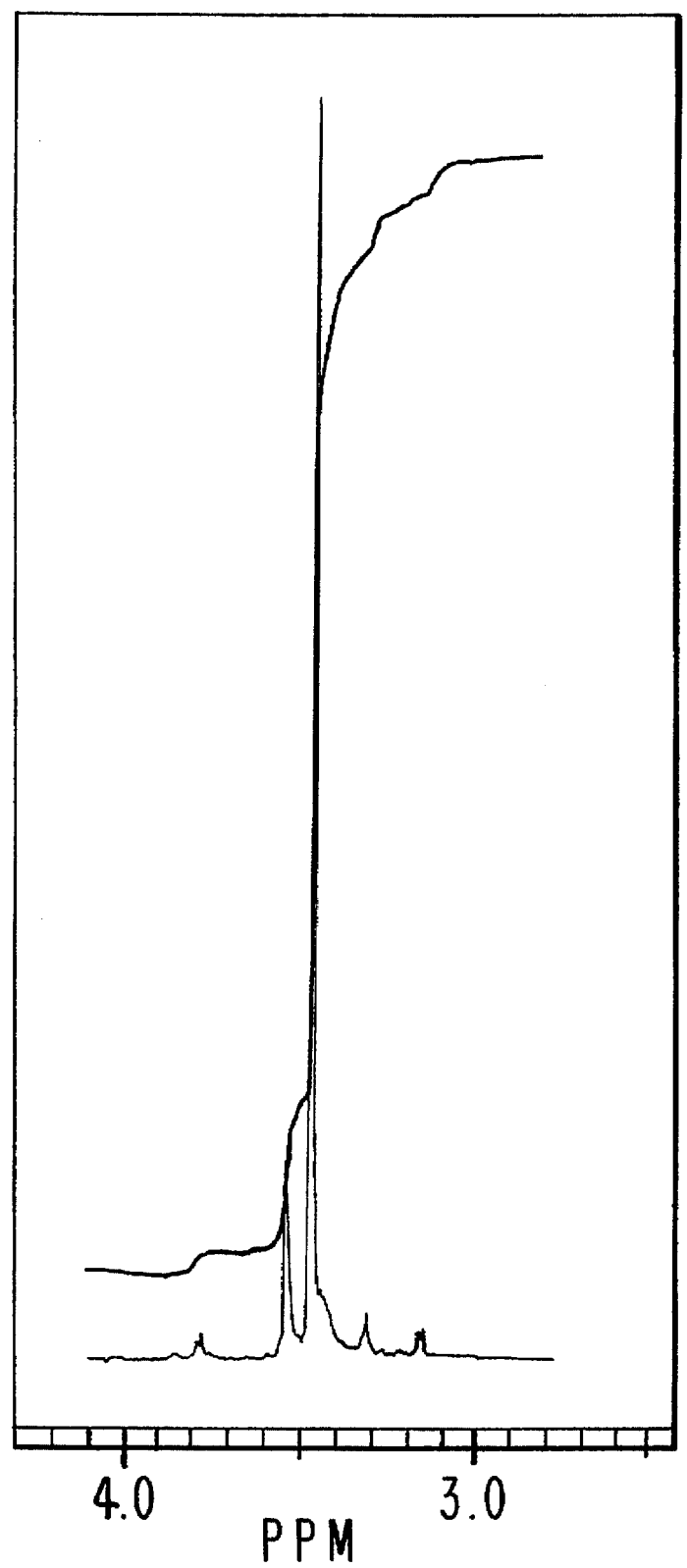

FIG. 3B is an enlargement of section "B" of the NMR spectrum of FIG. 3.

Figure 4:
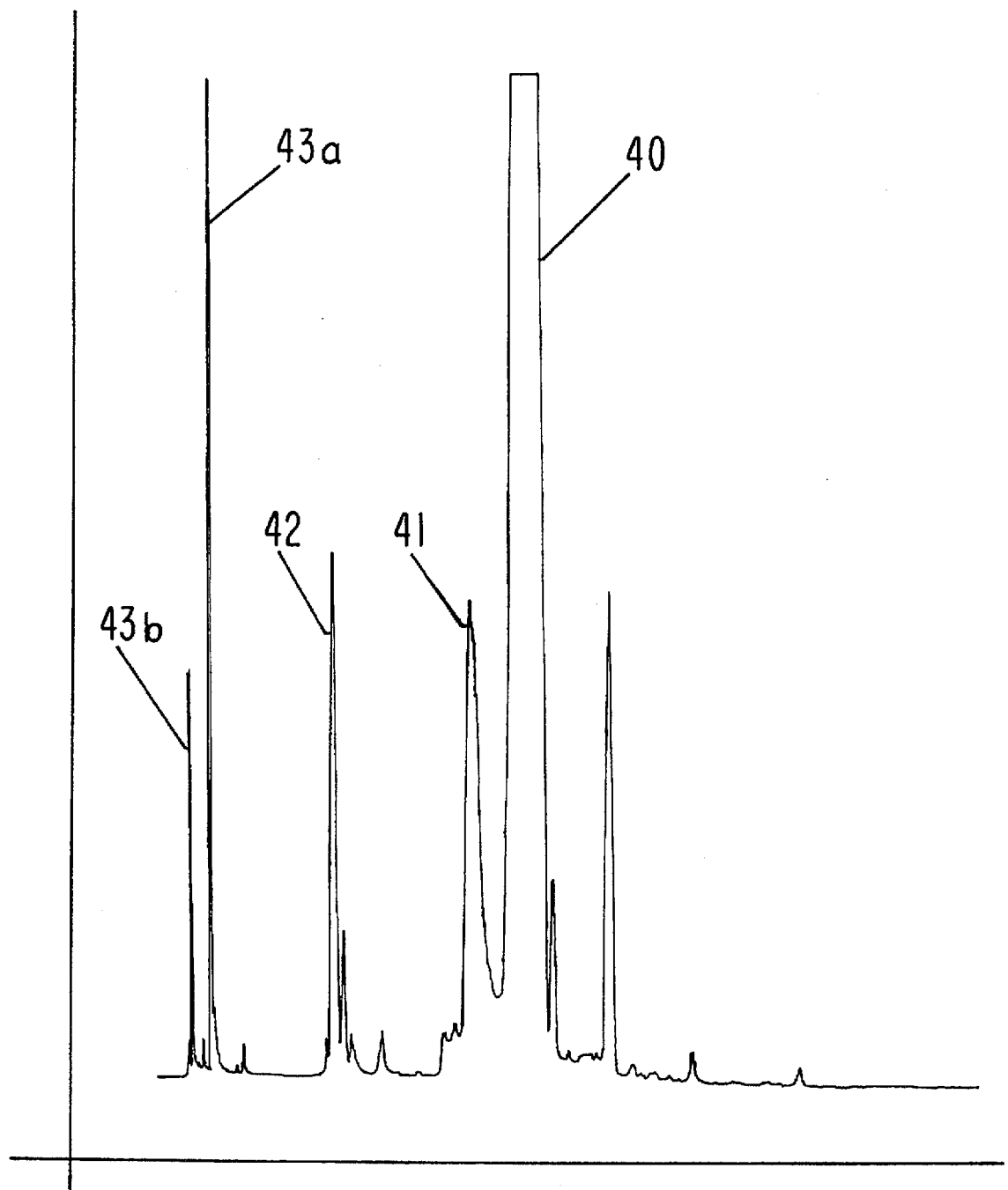

FIG. 4 is the GLC profile for the reaction product of Example II containing a mixture of compounds defined according to the structure:

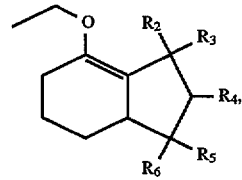

which is a mixture of compounds having the structures:

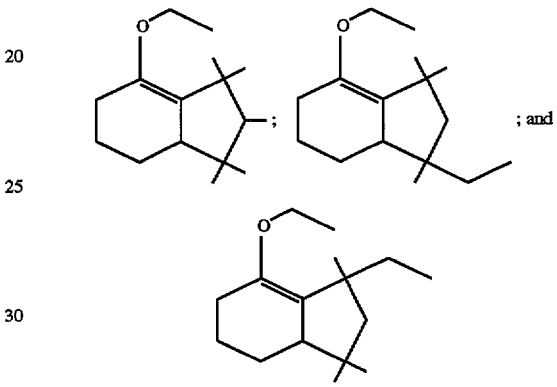

(conditions: SE-30 column programmed from 100°–220° C. at 8° C. per minute).

FIG. 5 is the NMR spectrum for the mixture of compounds having the structures:

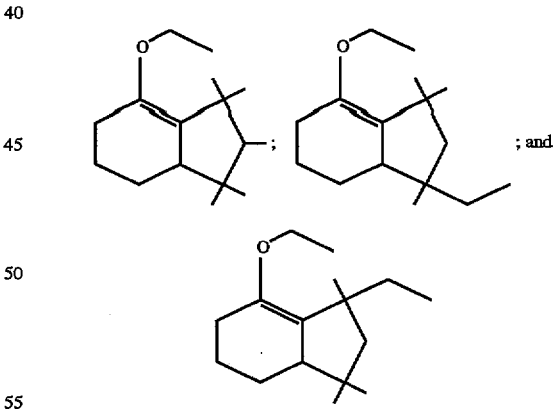

prepared according to Example II.

Figure 5A:
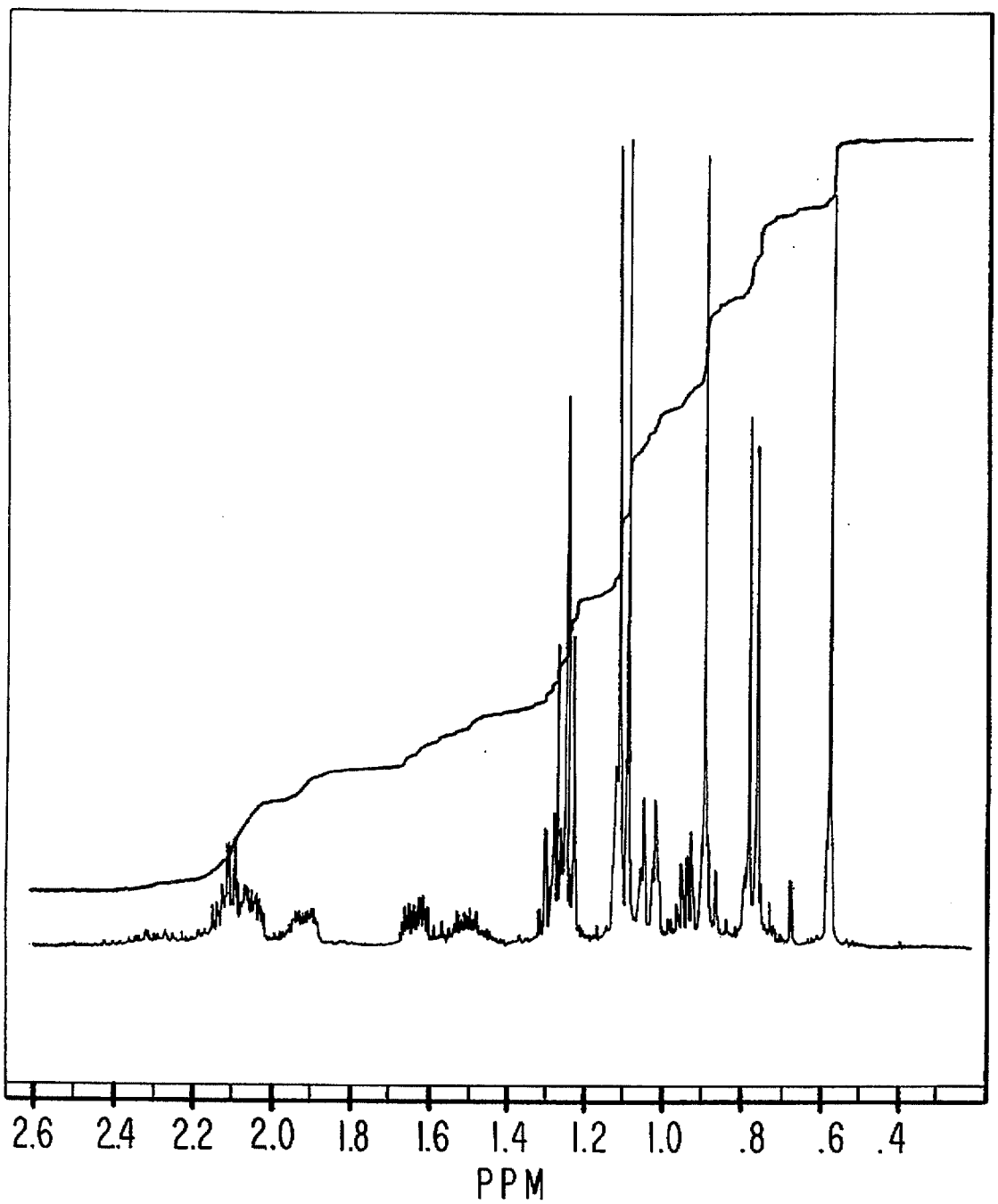

FIG. 5A is an enlargement of section "A" of the NMR spectrum of FIG. 5.

Figure 5B:
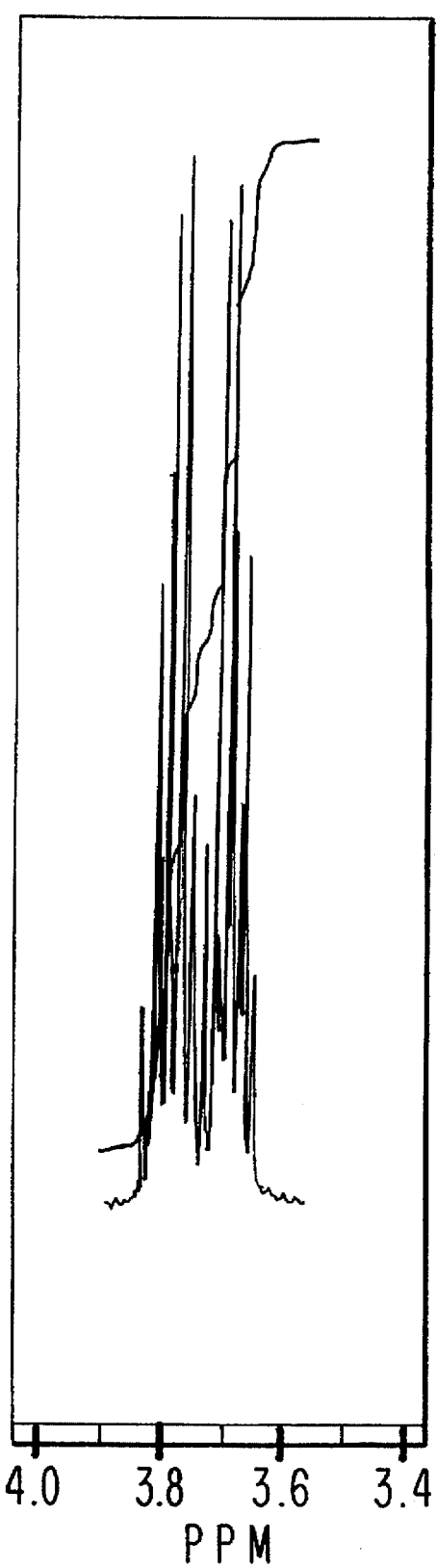

FIG. 5B is an enlargement of section "B" of the NMR spectrum of FIG. 5.

Figure 6:
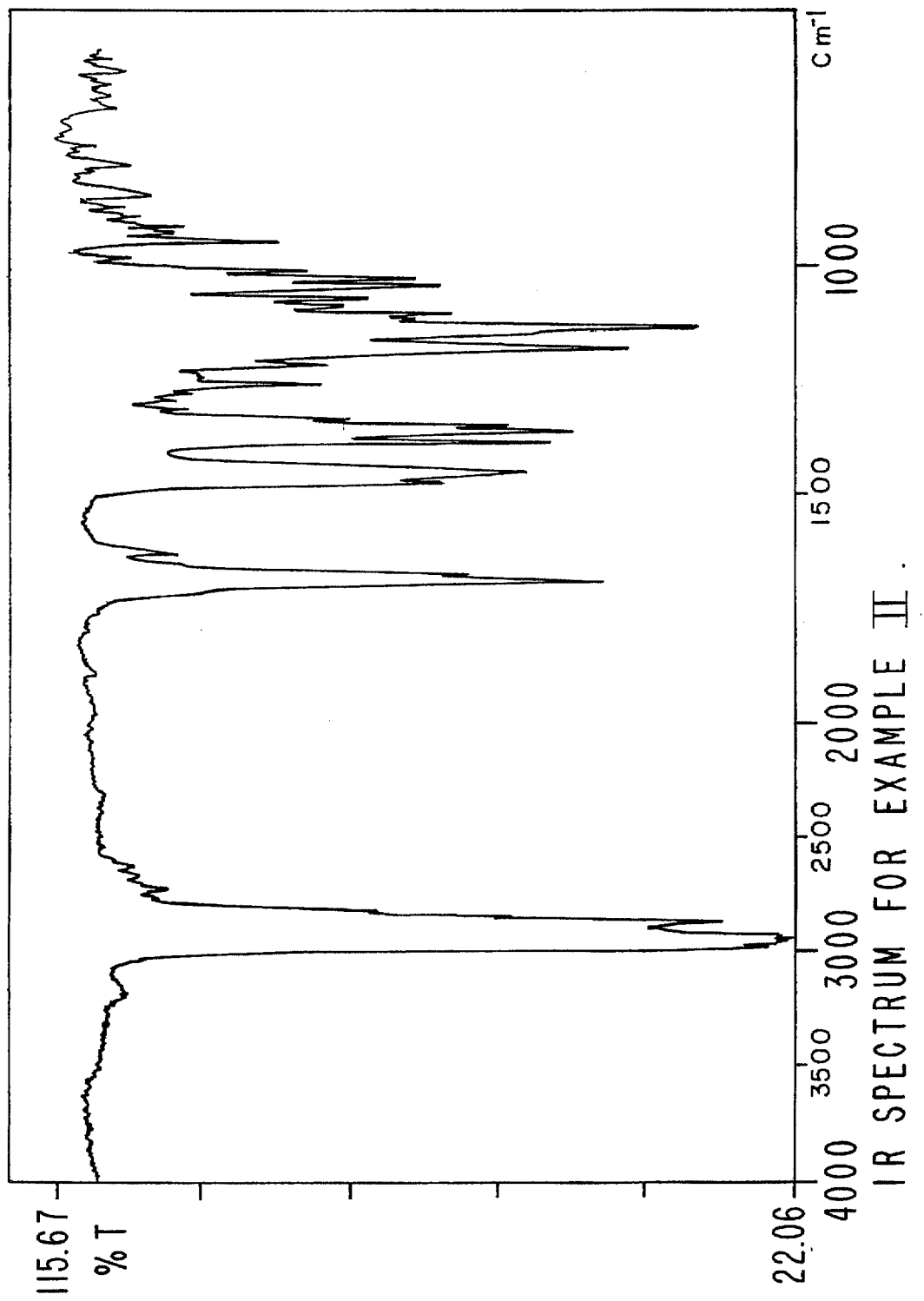

FIG. 6 is the IR spectrum (infrared spectrum) of the reaction product of Example II which is a mixture of compounds having the structures:

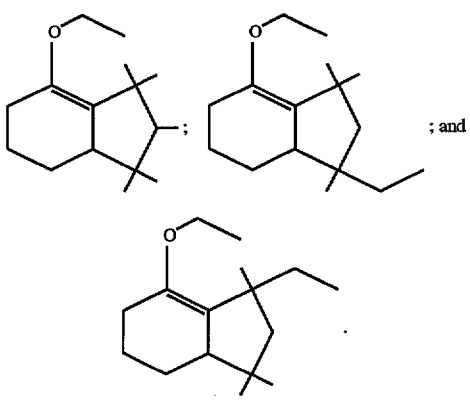

FIG. 7 is a partial side elevation and partial sectional view of an apparatus for forming scented polymers using at least one of the methyl substituted tetrahydroindane alkyl enol ethers of our invention.

FIG. 8 is a section taken along line 8—8 of FIG. 7.

DETAILED DESCRIPTION OF THE DRAWINGS

Referring to FIG. 1, the GLC profile of the reaction product of Example I, the peak indicated by reference numeral 10 is the peak for the mixture of compounds defined according to the structures:

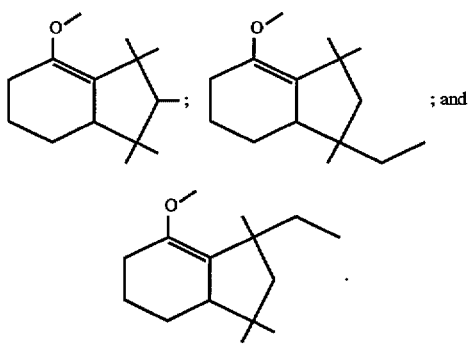

The peak indicated by reference numeral 41 is the peak for the mixture of starting materials defined according to the structures:

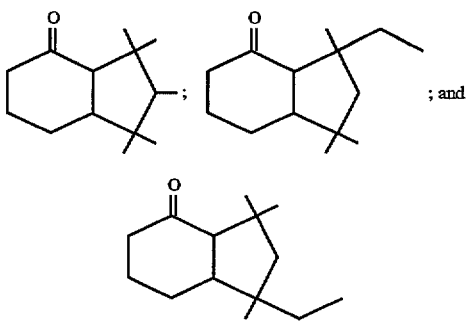

or defined according to the structure:

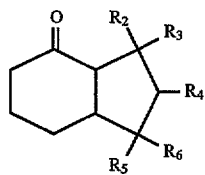

wherein $R_2$, $R_3$, $R_4$, $R_5$ and $R_6$ are defined, supra.

The peak indicated by reference numeral 42 is the peak for the hydrocarbon by-product having the structure:

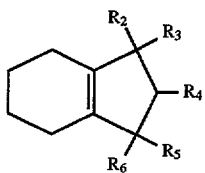

which is a mixture of compounds wherein $R_2$, $R_3$, $R_4$, $R_5$ and $R_6$ are defined, supra. The peaks indicated by reference numerals 12a and 12b are peaks for the reaction solvent, methyl alcohol.

Referring to FIG. 4, the GLC profile for the reaction product of Example II, the peak indicated by reference numeral 40 is the peak for the mixture of compounds having the structures:

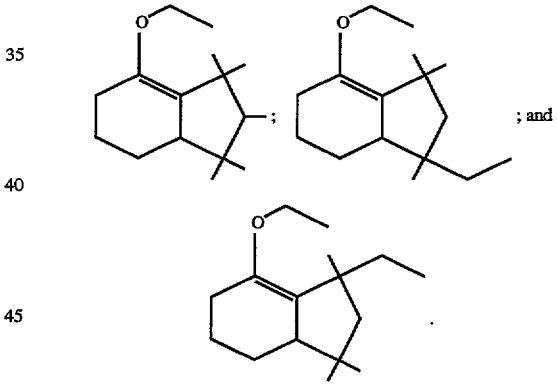

The peak indicated by reference numeral 41 is the peak for the starting material, the mixture of compounds having the structures:

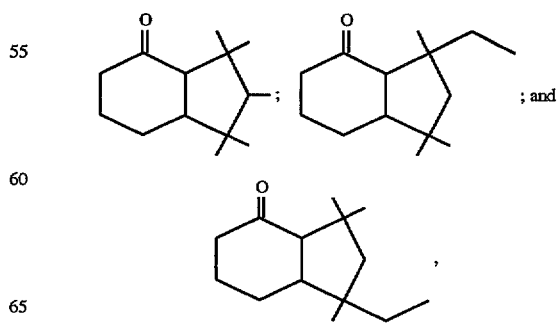

also shown by the structure:

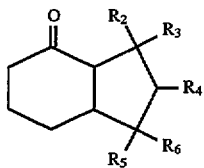

wherein $R_2$, $R_3$, $R_4$, $R_5$ and $R_6$ are defined, supra.

The peak indicated by reference numeral 42 is the peak for the mixture of hydrocarbons, a side product defined according to the structure:

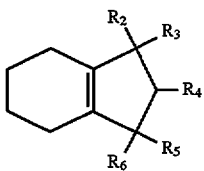

wherein $R_2$, $R_3$, $R_4$, $R_5$ and $R_6$ are defined, supra.

The peaks indicated by reference numerals 43a and 43b are peaks for the reaction solvent, ethyl alcohol.

Referring to the drawings in FIGS. 7 and 8, the invention embodied therein comprises a device for forming scented polymer pellets (e.g., polyethylene, polypropylene or mixtures such as polyepsiloncaprolactone and polyethylene or polypropylene or copolymers of polyvinyl acetate and polyethylene or the like) which comprises a vat or container 210 into which a polymer or mixture of polymers admixed with one of the methyl substituted tetrahydroindane alkyl enol ethers of our invention is placed.

The container is closed by an airtight lid 228 clamped to the container by clamps 265. A stirrer 273 traverses the lid or cover 228 in an airtight manner and is rotated in a suitable manner. The surrounding cylinder 212 having heating coils which are supplied with electrical current through cable 214 from a rheostat or control 216 is operated to maintain the temperature inside the container 210 such that the polymer such as polyethylene in the container will be maintained in a molten or liquid state. It has been found advantageous to employ a colorless, odorless polymer such as low density. polyethylene with a viscosity ranging between 180 and about 220 centistokes and having a melting point in the neighborhood of 220° F. The heater 212 is operated to maintain the upper portion of the container 210 within the temperature range of from 250°–350° F. An additional bottom heater is regulated through a control 220 connected thereto through a connecting wire 222 to maintain the lower portion of the container 210 within the temperature range of from 250°–350° F.

In accordance with this aspect of the invention, a polymer such as polyethylene or polypropylene is added to the container 210 and is then heated from 10 to 12 hours, whereafter an aroma imparting material containing at least one of the methyl substituted tetrahydroindane alkyl enol ethers of our invention is quickly added to the melt. The mixture containing one of the methyl substituted tetrahydroindane alkyl enol ethers of our invention must be compatible with the poller and forms a homogeneous liquid melt therewith. The heat resisting mixture generally containing from 10 to 40% of the mixture of at least one of the methyl substituted tetrahydroindane alkyl enol ethers of our invention is added to container 210; the mixture is stirred for a few minutes, for example, 5–15 minutes, and maintained within the temperature range as indicated previously by the heating coils 212. The controls 216 and 220 are connected through cables 224 and 226 through a suitable supply of electric current for supplying the power for heating purposes.

Thereafter, the valve "V" is opened permitting the mass to flow outwardly through a conduit 232 (also shown by reference numeral 218 (cutaway cross section)) having a multiplicity of orifices 234 adjacent to the lower side therof. The outer end of the conduit 232 is closed so that the liquid polymer and at least one of the methyl substituted tetrahydroindane alkyl enol ethers of our invention or a mixture containing same will continuously drop or drip through the orifices 234 downwardly from the conduit 232. During this time, the temperature of the polymer and the perfumant mixture containing at least one of the methyl substituted tetrahydroindane alkyl enol ethers of our invention in the container 210 is accurately controlled so that a temperature in the range of from 210° F. up to 275° F. will be maintained in the material exiting in the conduit 232. The regulation of the temperature through the control 216 and the control 220 is essential in order to insure temperature balance to provide for the continuous dropping or dripping of the molten polymer and the perfumant containing at least one of the methyl substituted tetrahydroindane alkyl enol ethers of our invention through the orifices 234 at a range which will insure the fomation of droplets 236 which will fall downwardly onto a moving conveyor belt 238 trained to run between conveyor wheels 240 and 242 beneath the conduit 232. When the droplets 236 fall onto the conveyor belt 238, they form pellets 244 which harden almost instantaneously and fall off the end of the conveyor 238 into a container 246 which is advantageously filled with water or some other suitable liquid to insure the rapid cooling of each of the pellets. The pellets are then collected from the container 246 and packaged for shipment or used to fabricate such articles of manufacture as fragranced garbage bags.

A feature of the invention is the provision for the moistening of the conveyor belt 238 to insure the rapid formation of the solid polymer-aromatizing agent containing pellets 244 without sticking to the belt. The belt 238 is advantageously of a material which will not normally stick to a melted polymer, but the moistening means 248 insures a sufficiently cold temperature of the belt surface for the adequate formation of the pellets 244. The moistening means comprises a container 250 which is continuously fed with water 254 to maintain a level 252 for moistening a sponge element 256 which bears against the exterior surface of the belt 238.

THE INVENTION

The present invention provides methyl substituted tetrahydroindane alkyl enol ethers defined according to the generic structure:

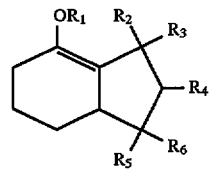

wherein $R_1$ represents methyl or ethyl; wherein $R_4$ represents methyl or hydrogen; wherein $R_2$, $R_3$, $R_5$ and $R_6$ each represents the same or different methyl or ethyl with the provisos that:

(1) at least three of $R_2$, $R_3$, $R_5$ and $R_6$ is methyl; and (2) when each of $R_2$, $R_3$, $R_5$ and $R_6$ is methyl, then $R_4$ is methyl.

The methyl substituted tetrahydroindane alkyl enol ethers of our invention have utilities in perfumery; that is in augmenting, enhancing or imparting an aroma in or to perfume compositions, colognes and perfumed articles including but not limited to solid or liquid anionic, cationic, nonionic or zwitterionic detergents, fabric softener compositions, fabric softener articles, cosmetic powders, hair preparations and perfumed polymers.

The methyl substituted tetrahydroindane alkyl enol ethers of our invention are prepared by reacting the mixture of ketones defined according to the structures:

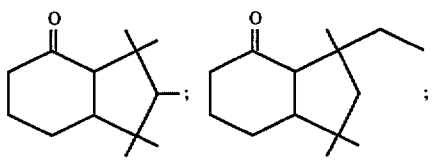

and

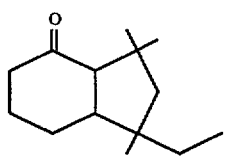

(otherwise shown by the structure:

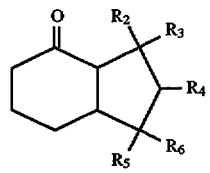

wherein $R_2$, $R_3$, $R_4$, $R_5$ and $R_6$ are defined, supra) with a trialkyl orthoformate defined according to the structure:

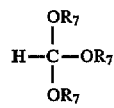

or defined according to the structure:

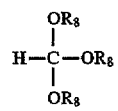

or a mixture thereof (shown by the structure:

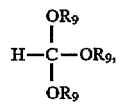

wherein $R_7$, $R_8$ and $R_9$ are methyl or ethyl. The reaction first enables the formation of the ketal having the structure:

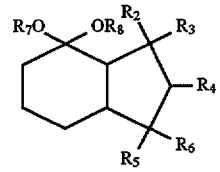

wherein $R_7$ and $R_8$ are the same or different methyl or ethyl. Thus, if a mixture of triethyl orthoformate and trimethyl orthoformate are reacted with the mixture of ketones defined according to the structure:

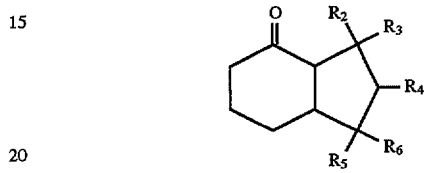

then a mixture of diethyl ketals, dimethyl ketals and ethyl-methyl ketals is formed. Obviously, if only trimethyl orthoformate is used as a reactant, then the dimethyl ketals will be formed; and if only triethyl orthoformate is used as a reactant, then only the diethyl ketals are formed.

Further reaction causes the rearrangement of the ketal having the structure:

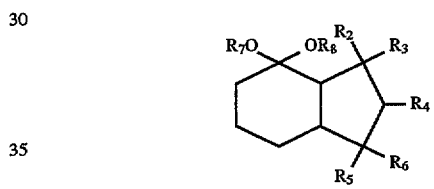

to the enol ether defined according to the structure:

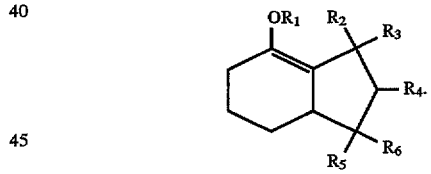

The reactions are shown thusly:

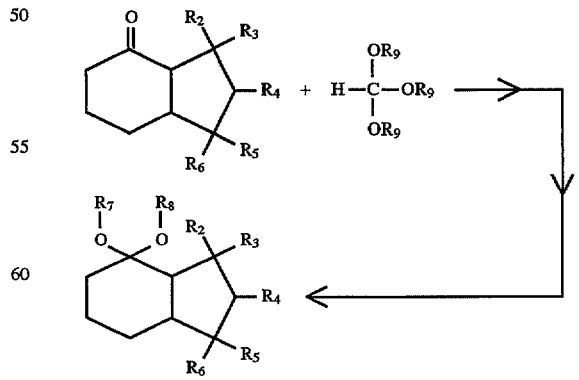

and

-continued

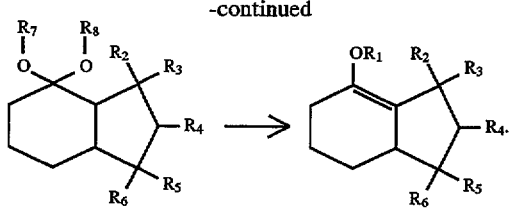

The reaction takes place in the presence of an acid ion exchange catalyst, for example, AMBERLYST® 15 (trademark of the Rohm and Haas Company of Philadelphia, Penn.). The temperature of reaction is initially from about $-5°$ C. up to about $10°$ C. for the reaction:

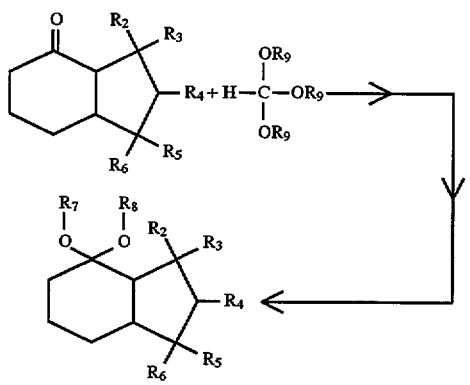

to take place; and then from about $20°$ C. up to about $50°$ C. for the reaction:

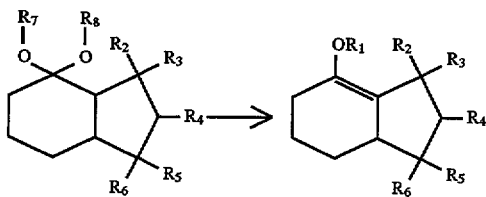

to take place.

The time of reaction for the first reaction:

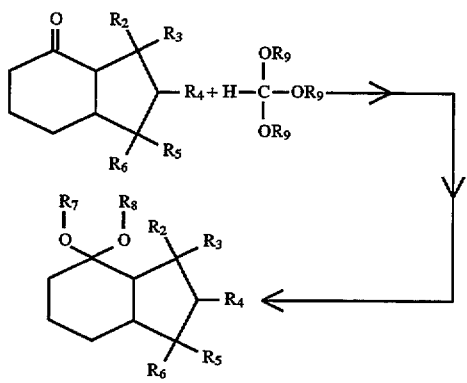

is between about 5 hours up to about 10 hours.

The time of reaction for the reaction:

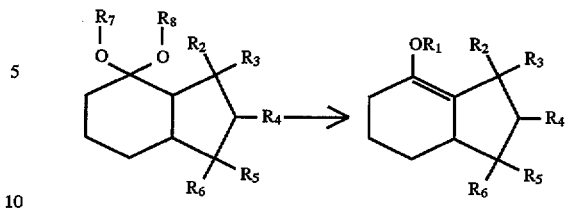

to take place is from about 7 hours up to about 15 hours.

The reaction takes place in a solvent and preferred solvents are lower alkanols. When the methyl ether is desired to be formed, then the solvent is methyl alcohol. When the ethyl ether is desired to be formed, then the solvent is ethyl alcohol. When mixtures of the methyl ether and the ethyl ether are desired to be formed, then the preferred solvent is a mixture of methyl alcohol and ethyl alcohol.

The weight ratio of ketone mixture defined according to the structure:

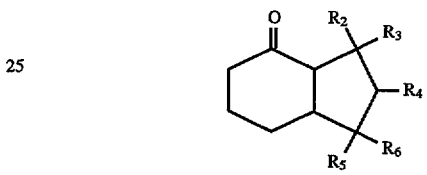

to trialkyl orthoformate having the structure:

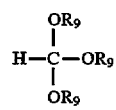

is approximately and preferably 1:1. The amount of ion exchange catalyst in the reaction mass is between about 1% by weight of the reaction mass up to about 5% by weight of the reaction mass (on a solvent-free basis). The amount of methanol and/or ethanol solvent (based on the weight of solvent-free reaction mass) may vary from about 0.1 liters per kilogram up to about 1 liter per kilogram with a preferred solvent quantity of about 0.2 liters per kilogram.

Immediately upon the cessation of the reaction and after the solvent is stripped, the reaction mass is washed in order to purify it by means of ordinary "work-up" techniques; and then the reaction mass is distilled to yield the odor acceptable fraction or fractions for use for their respective organoleptic properties.

Examples of the methyl substituted tetrahydroindane alkyl enol ethers of our invention produced according to the processes of our invention and their organoleptic properties are set forth in the following Table I:

TABLE I

| Structure of The Methyl Substituted Tetrahydroindane Alkyl Enol Ethers of Our Invention | Perfumery Evaluation |
|---|---|
| The mixture of compounds having the structures: | A sweet, musky aroma with woody, balsamic, amber, powdery, sweet and musky topnotes. |

TABLE I-continued

| Structure of The Methyl Substituted Tetrahydroindane Alkyl Enol Ethers of Our Invention | Perfumery Evaluation |
|---|---|
| 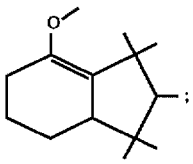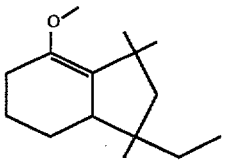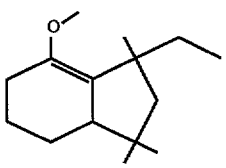 produced according to Example I, bulked distillation fractions 13–20. The mixture of compounds having the structures: | |
| 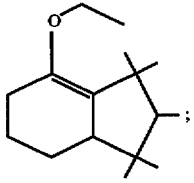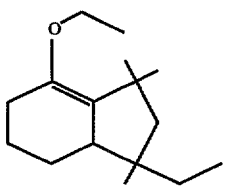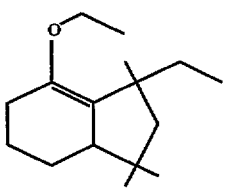 produced according to Example II, bulked distillation fractions 10–20. | A woody, sweet, musky, balsamic and amber aroma. |

One or more of the methyl substituted tetrahydroindane alkyl enol ethers of our invention and one or more auxiliary perfume ingredients including alcohols, aldehydes, ketones, ethers other than the methyl substituted tetrahydroindane alkyl enol ethers of our invention, esters, terpenic hydrocarbons, nitriles, lactones, natural essential oils and synthetic essential oils may be admixed so that the combined odors of the individual components produce a pleasant and desired fragrance, particularly in the musk, amber and patchouli fragrance classes.

Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low-boiling, fresh smelling materials.

In perfume compositions, it is the individual components which contribute to their particular olfactory characteristics; however, the overall sensory effect of the perfume composition will be at least the sum total of the effects of each of the ingredients. Thus, one or more of the methyl substituted tetrahydroindane alkyl enol ethers of our invention can be used to alter, modify or enhance the aroma characteristics of a perfume composition, for example, by utilizing or moderating the olfactory reaction contributed by another ingredient in the composition.

The amount of one or more of the methyl substituted tetrahydroindane alkyl enol ethers of our invention which will be effective in perfume compositions as well as in perfumed articles and colognes depends on many factors including the other ingredients, their amounts and the effects which are desired. It has been found that perfume compositions containing as little as 0.01% of one or more of the methyl substituted tetrahydroindane alkyl enol ethers of our invention and or even less (e.g., 0.005%) can be used to augment or enhance or impart sweet, musky, woody, balsamic and amber aromas with woody, balsamic, amber, powdery, sweet and musky topnotes to soaps, cosmetics, solid or liquid anionic, cationic, nonionic or zwitterionic detergents, powders, fabric softeners, drier-added fabric softener articles, hair conditioners and colognes. The amount employed can range up to 70% of the fragrance components and will depend upon considerations of cost, nature of the end product, the effect desired on the finished product and the particular fragrance sought.

The methyl substituted tetrahydroindane alkyl enol ethers of our invention are useful (taken alone or taken further together with other ingredients in perfume compositions) as (an) olfactory component(s) in detergents and soaps, space odorants and deodorants, perfumes, colognes, toilet water, bath preparations such as lacquers, brilliantines, pomades and shampoos; cosmetic preparations such as creams, deodorants, hand lotions and sun screens; powders such as talcs, dusting powders, face powders and the like. When used as (an) olfactory component(s), as little as 1% of the methyl substituted tetrahydroindane alkyl enol ethers of our invention will suffice to impart intense and long-lasting sweet, musky, woody, balsamic and amber aromas with woody, balsamic, amber, powdery, sweet and musky topnotes to various formulations such as patchouli formulations. Although generally no more than 60% of the methyl substituted tetrahydroindane alkyl enol ethers of our invention based on the ultimate end product is required in the perfume composition, amounts of at least one of the methyl substituted tetrahydroindane alkyl enol ethers of our invention of up to 95% may be used in such perfume compositions.

When used in perfumed articles such as solid or liquid anionic, cationic, nonionic or zwitterionic detergents or drier added fabric softener articles, cosmetic powders or deodorant compositions, from 0.1 up to 5.0% of at least one of the methyl substituted tetrahydroindane alkyl enol ethers of our invention based on the overall perfumed article weight may be used in the perfumed articles to impart intense and long-lasting sweet, musky, woody, balsamic and amber aromas with woody, balsamic, amber, powdery, sweet and musky topnotes.

In addition, the perfume compositions of our invention can contain a vehicle or carrier for at least one of the methyl substituted tetrahydroindane alkyl enol ethers of our invention taken alone or taken together with other ingredients. The vehicle can be a liquid such as an alcohol such as ethanol, a non-toxic glycol such as propylene glycol or the like.

The carrier can be an absorbent solid such as a gum (e.g., xanthan gum, gum arabic, guar gum or mixtures therof) or components for encapsulating the composition as by coacervation in gelatin or by forming a polymeric shell around a liquid perfume center by means of the use of, for example, a ureaformaldehyde prepolymer.

The following Examples I and II set forth processes for preparing the methyl substituted tetrahydroindane alkyl enol ethers of our invention. Example III, et seq., set forth methods for using the methyl substituted tetrahydroindane alkyl enol ethers of our invention for their organoleptic properties.

Unless otherwise indicated, all parts and percentages are by weight.

EXAMPLE I

PREPARATION OF 3a,4,5,6-TETRAHYDRO-7-METHOXY-1,1,3,3-PENTA ALKYL SUBSTITUTED INDANE MIXTURE

Reactions:

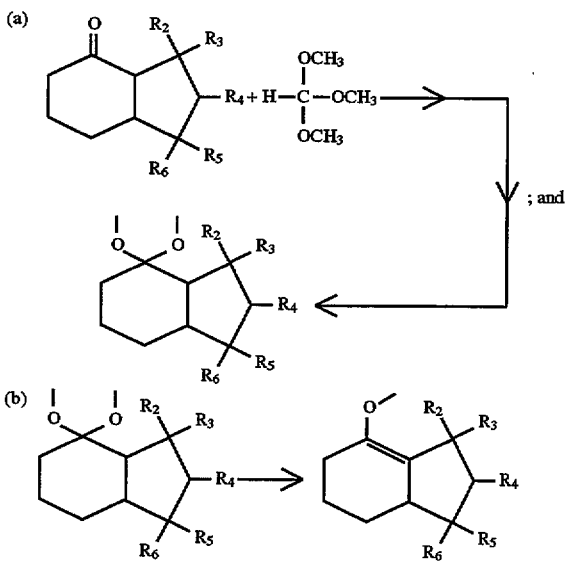

(wherein $R_2$, $R_3$, $R_4$, $R_5$ and $R_6$ are defined, supra).

Into a 5 liter reaction vessel equipped with stirrer, thermometer, cooling coils and heating mantle as well as reflux condenser are placed the following ingredients:

(a) the mixture of compounds having the structures:

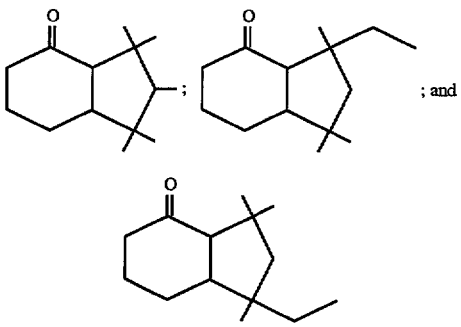

... 1,664 grams;

(b) trimethyl orthoformate having the structure:

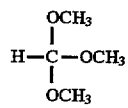

... 1,696 grams; and (c) methyl alcohol ... 600 mL.

The resulting mixture is cooled, with stirring, to −5° C.

67 Grams of AMBERLYST® 15 (ion exchange catalyst) (trademark of the Rohm and Haas Company of Philadelphia, Penn.) is then added to the reaction mass while maintaining the reaction temperature at −5° C. The reaction mass is then maintained at −5° C. for a period of 2 hours whereupon the temperature of the reaction mass is raised over a period of 5 hours to 10° C. and maintained at 10° C. for 8 more hours.

The temperature of the reaction mass is then raised to 22°–23° C. and maintained at 22°–23° C. for a period of 6 hours. At the end of the 6 hour period, the reaction mass is heated to 45° C. and maintained at 45° C. for a period of 2 hours.

The reaction mass is then admixed with 300 grams of a 25% aqueous solution of sodium hydroxide. The reaction mass now exists in two phases: an aqueous phase and an organic phase. The organic phase is separated from the aqueous phase and the organic phase is filtered through anhydrous sodium sulfate and then washed as follows:

(a) 1 liter saturate a sodium bicarbonate; and (b) 1 liter water.

The resulting product is then filtered through anhydrous sodium sulfate yielding 64% product.

The reaction mass is then fractionally distilled yielding the following fractions:

| Fraction Number | Vapor Temperature (°C.) | Liquid Temperature (°C.) | Vacuum mm/Hg Pressure |
|---|---|---|---|
| 1 | 29/30 | 46/80 | 180/240 |
| 2 | 57 | 106 | 2.05 |
| 3 | 98 | 106 | 1.82 |
| 4 | 121/109 | 195 | 4.5 |

Fractions 2–4 are bulked and redistilled yielding 25 fractions. Fractions 13–20 distilling at a vapor temperature of 95°–100° C. and a liquid temperature of 106° C. at a pressure of 1.7–1.9 mm/Hg are bulked. The bulked fractions have sweet and musky aromas with woody, balsamic, amber, powdery, sweet and musky topnotes.

EXAMPLE II

PREPARATION OF 7-ETHOXY-3a,4,5,6-TETRAHYDRO-1,1,3,3,-TETRA ALKYL SUBSTITUTED INDANE

Reactions:

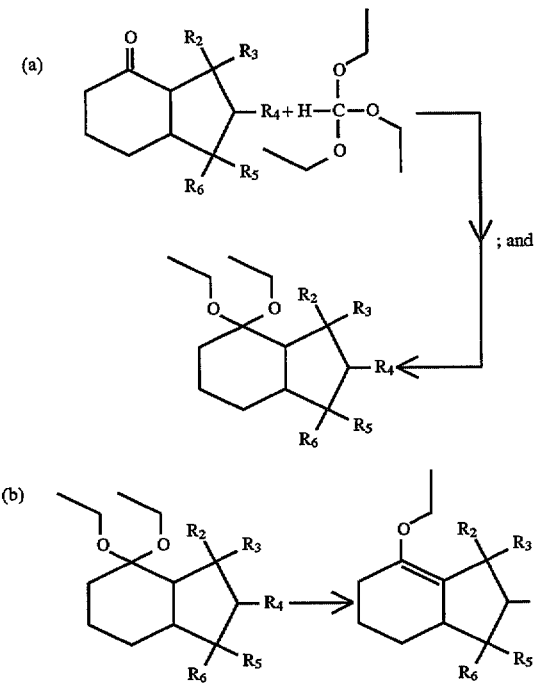

Into a 2 liter reaction flask equipped with stirrer, thermometer, reflux condenser and cooling coils are placed the following materials:

(a) the mixture of compounds having the structures:

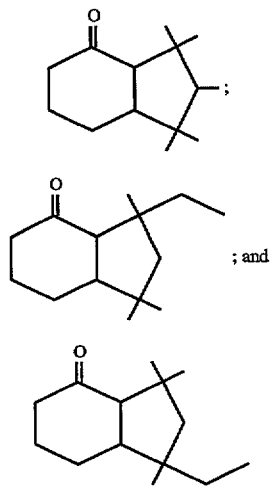

. . . 416 grams;

(b) triethyl orthoformate having the structure:

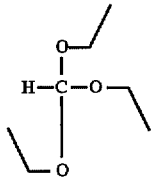

. . . 592 grams; and (c) ethyl alcohol . . . 200 ml.

The reaction mass is cooled to 10° C.

While maintaining the reaction mass at 10° C., 12 grams of AMBERLYST® 15 catalyst is added to the reaction mass with stirring (AMBERLYST® 15 is a trademark of the Rohm and Haas Company of Philadelphia, Penn.; it is an acid ion exchange catalyst.

The reaction mass is heated to 24°–26° C. with stirring and maintained at 24°–26° C. for a period of 4.5 hours.

At the end of the 4.5 hour period, the reaction mass is filtered through anhydrous sodium sulfate:sodium acetate (50:50). The resulting yield is 63%.

The reaction mass is then fractionally distilled yielding the following fractions:

| Fraction Number | Vapor Temperature (°C.) | Liquid Temperature (°C.) | Vacuum mm/Hg Pressure |
|---|---|---|---|
| 1 | 37/100 | 95/119 | 7.60/1.26 |
| 2 | 120 | 109 | 2.78 |
| 3 | 112 | 190 | 3.14 |

Fractions 2 and 3 are bulked and redistilled. The resulting distillation product contains 25 fractions of which fractions 10–20 are bulked. Fractions 10–20 distill at a vapor temperature of 120° C. and at a liquid temperature of 130° C. at a vacuum of 2.7–2.9 mm/Hg. The resulting bulked fractions have a woody, sweet, musky, balsamic and amber aroma.

EXAMPLE III

Woody fragrance formulations are prepared using products prepared according to Examples I and/or II:

| Ingredients | Parts by Weight | | |
|---|---|---|---|
| | III(A) | III(B) | III(C) |
| Vetiver oil | 40 | 40 | 40 |
| Ethyl alcohol | 60 | 60 | 60 |
| Sandalwood oil E.I. | 100 | 100 | 100 |
| Rose geranium oil | 200 | 200 | 200 |
| Civetone | 25 | 25 | 25 |
| Benzyl isoeugenol | 100 | 100 | 100 |
| Coumarin | 100 | 100 | 100 |
| Heliotropin | 50 | 50 | 50 |
| Bois de rose oil | 200 | 200 | 200 |
| Benzoin resin | 100 | 100 | 100 |

| Ingredients | Parts by Weight | | |
|---|---|---|---|
| | III(A) | III(B) | III(C) |
| The mixture of compounds having the structures: 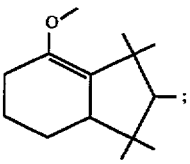 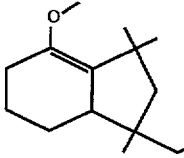 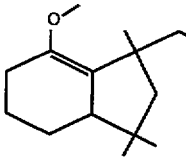 produced according to Example I, bulked distillation fractions 13–20. | 20 | 0 | 0 |
| The mixture of compounds having the structures: 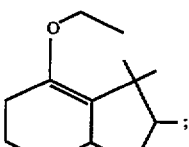 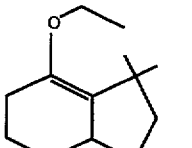 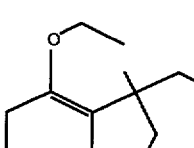 prepared according to Example II, bulked distillation fractions 10–20. 50:50 Mixture of compounds having the structures: 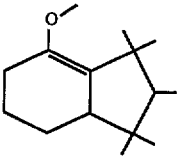 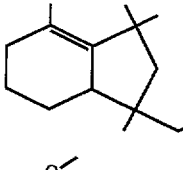 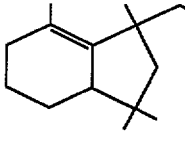 prepared according to Example I, bulked distillation fractions 13–20 and the mixture of compounds having the structures: 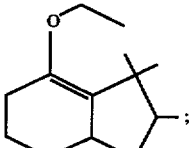 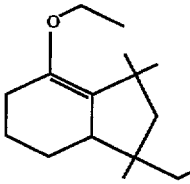 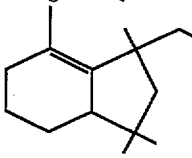 prepared according to Example II, bulked distillation fractions 10–20. | 0 | 20 | 0 |
| | 0 | 0 | 20 |

The product of Example I imparts to the woody perfume formulation sweet and musky undertones with balsamic, amber, powdery, sweet and musky topnotes. Accordingly, the perfume of Example III(A) can be described as follows:

a woody aroma with sweet and musky undertones and balsamic, amber, powdery, sweet and musky topnotes.

The product of Example II imparts to this woody perfume formulation sweet, musky, balsamic and amber undertones. Accordingly, the perfume composition of Example III(B) can be described as follows:

a woody aroma with sweet, musky, balsamic and amber undertones.

The 50:50 mixture of the products of Examples I and II impart to this woody perfume formulation sweet, musky, balsamic and amber undertones and balsamic, amber, powdery, sweet and musky topnotes. Accordingly, the perfume composition of Example III(C) can be described as follows:

a woody aroma with sweet, musky, balsamic and amber undertones and balsamic, amber, powdery, sweet and musky topnotes.

EXAMPLE IV

PREPARATION OF COSMETIC POWDER COMPOSITION

Cosmetic powder compositions are prepared by mixing in a ball mill 100 grams of talcum powder with 0.25 grams of each of the substances set forth in Table II below. Each of the cosmetic powder compositions has an excellent aroma as described in Table II below.

TABLE II

| Substance | Aroma Description |
|---|---|
| The mixture of compounds having the structures: 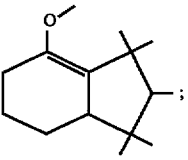 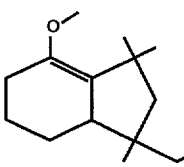 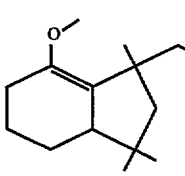 produced according to Example I, bulked distillation fractions 13–20. The mixture of compounds having the structures: 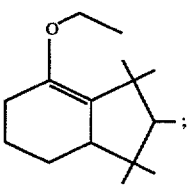 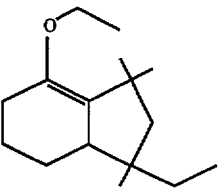 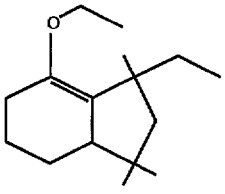 prepared according to Example II, bulked distillation fractions 10–20. | A sweet, musky aroma with woody, balsamic, amber, powdery, sweet and musky topnotes. |
| | A woody, sweet, musky, balsamic and amber aroma. |
| Perfume composition of Example III(A). | A woody aroma with sweet and musky undertones and balsamic, amber, powdery, sweet and musky topnotes. |
| Perfume composition of Example III(B). | A woody aroma with sweet, musky, balsamic and amber undertones. |
| Perfume composition of Example III(C). | A woody aroma with sweet, musky, balsamic and amber undertones and balsamic, amber, powdery, sweet and musky topnotes. |

EXAMPLE V

PERFUMED LIQUID DETERGENTS

Concentrated liquid detergents (lysine salt of n-dodecylbenzene sulfonic acid as more specifically described in U.S. Pat. No. 3,948,818 issued Apr. 6, 1976, incorporated by reference herein) with aroma nuances as set forth in Table II of Example IV are prepared containing 0.10%, 0.15%, 0.20%, 0.25%, 0.30% and 0.35% of the substance set forth in Table II of Example IV. They are prepared by adding and homogeneously mixing the appropriate quantity of substance set forth in Table II of Example IV in the liquid detergent. The detergents all possess excellent aromas as set forth in Table II of Example IV, the intensity increasing with greater concentrations of substance as set forth in Table II of Example IV.

EXAMPLE VI

PREPARATION OF COLOGNE AND HANDKERCHIEF PERFUMES

Compositions as set forth in Table II of Example IV, are incorporated into colognes at concentrations 2.0%, 2.5%, 3.0%, 3.5%, 4.0%, 4.5% and 5.0% in 80%, 85%, 90% and 95% aqueous food grade ethanol solutions; and into handkerchief perfumes at concentrations of 15%, 20%, 25% and 30% (in 80%, 85%, 90% and 95% aqueous food grade ethanol solutions). Distinctive and definite fragrances as set forth in Table II of Example IV are imparted to the colognes and to the handkerchief perfumes at all levels indicated.

EXAMPLE VII

PREPARATION OF A SOAP COMPOSITION

100 Grams of soap chips (per sample) (IVORY® produced by the Procter & Gamble Company of Cincinnati, Ohio) are each mixed with 1 gram samples of substances as set forth in Table II of Example IV until homogeneous compositions are obtained. In each of the cases, the homogeneous compositions are heated under 8 atmospheres pressure at 180° C. for a period of 3 hours and the resulting liquids are placed into soap molds. The resulting soap cakes, on cooling, manifest aromas as set forth in Table II of Example IV.

EXAMPLE VIII

PREPARATION OF SOLID DETERGENT COMPOSITIONS

Detergents are prepared using the following ingredients according to Example I of Canadian Patent No. 1,007,948 (incorporated by reference herein):

| Ingredient | Parts by Weight |
| --- | --- |
| NEODOL ® 45-11 (a $C_{14}$–$C_{15}$ alcohol ethoxylated with 11 moles of ethylene oxide) | 12 |
| Sodium carbonate | 55 |
| Sodium citrate | 20 |
| Sodium sulfate, water brighteners | q.s. |

This detergent is a phosphate-free detergent. Samples of 100 grams each of this detergent are admixed with 0.10, 0.15, 0.20 and 0.25 grams of each of the substances as set forth in Table II of Example IV. Each of the detergent samples has an excellent aroma as indicated in Table II of Example IV.

EXAMPLE IX

Utilizing the procedure of Example I of column 15 of U.S. Pat. No. 3,632,396 (the disclosure of which is incorporated herein by reference), non-woven cloth substrates useful as drier-added fabric softening articles of manufacture are prepared wherein the substrate, the substrate coating, the outer coating and the perfuming material are as follows:

1. a water "dissolvable" paper ("Dissolvo Paper");
2. Adogen 448 (m.p. about 140° F.) as the substrate coating; and
3. an outer coating having the following formulation (m.p. about 150° F.):
   57% $C_{20-22}$ HAPS;
   22% isopropyl alcohol;
   20% antistatic agent; and
   1% of one of the perfume materials as set forth in Table II of Example IV.

Fabric softening compositions prepared according to Example I at column 15 of U.S. Pat. No. 3,632,396 having a weight of about 3 grams per 100 square inches of substrate; a first coating located directly on the substrate coating consisting of about 1.85 grams per 100 square inches of substrate; and an outer coating coated on the first coating consisting of about 1.4 grams per 100 square inches of substrate. One of the substances of Table II of Example IV is admixed in each case with the outer coating mixture, thereby providing a total aromatized outer coating weight ratio to substrate of about 0.5:1 by weight of the substrate. The aroma characteristics are imparted in a pleasant manner to the head space in a drier on operation thereof in each case using said drier-added fabric softener, non-woven fabrics and these aroma characteristics are described in Table II of Example IV.

EXAMPLE X

Hair Spray Formulations

The following hair spray formulation is prepared by first dissolving PVP/VA E-735 copolymer manufactured by the GAF Corporation of 140 West 51st Street, New York, N.Y. in 91.62 grams of 95% food grade ethanol. 8.0 Grams of the polymer is dissolved in the alcohol. The following ingredients are added to the PVP/VA alcoholic solution:

| Ingredient | Weight Percent |
| --- | --- |
| Dioctyl sebacate | 0.05 |
| Benzyl alcohol | 0.10 |
| Dow Corning 473 fluid prepared by the Dow Corning Corporation | 0.10 |
| TWEEN ® surfactant (prepared by ICI America Corporation) | 0.03 |
| One of the perfumery substances as set forth in Table II of Example IV | 0.10 |

The perfuming substances as set forth in Table II of Example IV add aroma characteristics as set forth in Table II of Example IV which are rather intense and aesthetically pleasing to the users of the soft-feel, good-hold pump hair sprays.

EXAMPLE XI

Conditioning Shampoos

A Monamid CMA (prepared by the Mona Industries Company) (3.0 weight percent) is melted with 2.0 weight percent coconut fatty acid (prepared by the Procter & Gamble Company of Cincinnati, Ohio); 1.0 weight percent ethylene glycol distearate (prepared by the Armak Corporation) and triethanolamine (a product of the Union Carbide Corporation) (1.4 weight percent). The resulting melt is admixed with Stepanol WAT produced by the Stepan Chemical Company (35.0 weight percent). The resulting mixture is heated to 60° C. and mixed until a clear solution is obtained (at 60° C.). This material is "Composition A".

GAFQUAT® 755N polymer (manufactured by GAF Corporation of 140 West 51st Street, New York, N.Y.) (5.0 weight percent) is admixed with 0.1 weight percent sodium sulfite and 1.4 weight percent polyethylene glycol 6000 distearate produced by the Armak Corporation. This material is "Composition B".

The resulting "Composition A" and "Composition B" are then mixed in a 50:50 weight ratio of A:B and cooled to 45° C., and 0.3 weight percent of perfuming substance as set forth in Table II of Example IV is added to the the mixture. The resulting mixture is cooled to 40° C. and blending is carried out for an additional 1 Hour in each case. At the end of this blending period, the resulting material has a pleasant fragrance as indicated in Table II of Example IV.

What is claimed is:
1. A mixture of compounds defined according to structure:

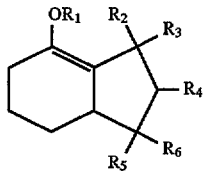

wherein $R_1$ is selected from the group consisting of methyl and ethyl; wherein $R_4$ represents methyl or hydrogen; wherein $R_2$, $R_3$, $R_5$ and $R_6$ each represents methyl or ethyl with the provisos that:

(1) at least three of $R_2$, $R_3$, $R_5$ and $R_6$ represent methyl; and (2) when each of $R_2$, $R_3$, $R_5$ and $R_6$ is methyl, then $R_4$ is methyl.

2. The mixture of claim 1 wherein $R_1$ is methyl.

3. The mixture of claim 1 wherein $R_1$ is ethyl.

4. A process for augmenting or enhancing the aroma of a perfume composition, cologne or perfumed article comprising the step of intimately admixing with a perfume base, a cologne base or a perfumed article base an aroma augmenting or enhancing quantity of the composition of matter defined according to claim 1.

5. A process for augmenting or enhancing the aroma of a perfume composition, cologne or perfumed article comprising the step of intimately admixing with a perfume base, a cologne base or a perfumed article base an aroma augmenting or enhancing quantity of the composition of matter defined according to claim 2.

6. A process for augmenting or enhancing the aroma of a perfume composition, cologne or perfumed article comprising the step of intimately admixing with a perfume base, a cologne base or a perfumed article base an aroma augmenting or enhancing quantity of the composition of matter defined according to claim 3.

7. A perfume composition consisting of a perfume base and intimately admixed therewith an aroma augmenting or enhancing quantity and concentration of the composition of matter defined according to claim 1.

8. A perfumed article consisting of a perfumed article base and intimately admixed therewith an aroma augmenting or enhancing quantity and concentration of a composition of matter defined according to claim 1.

9. A cologne consisting of alcohol, water and an aroma imparting quantity of a composition of matter defined according to claim 1.

10. A mixture of compounds defined according to the structure:

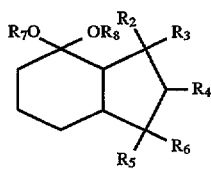

wherein $R_7$ and $R_8$ are the same or different methyl or ethyl; wherein $R_4$ represents methyl or hydrogen; wherein $R_2$, $R_3$, $R_5$ and $R_6$ each represents methyl or ethyl with the provisos that:

(1) at least three of $R_2$, $R_3$, $R_5$ and $R_6$ represent methyl; and (2) when each of $R_2$, $R_3$, $R_5$ and $R_6$ is methyl, then $R_4$ is methyl.

11. A process for forming a composition of matter defined according to the structure:

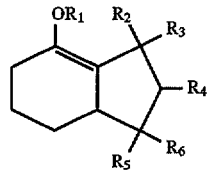

comprising the step of intimately admixing the compound defined according to the structure:

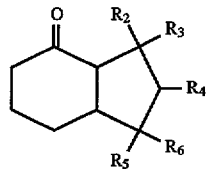

with the compound defined according to the structure:

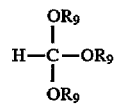

in order to form the compound having the structure:

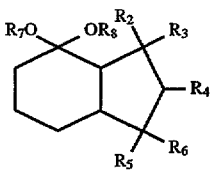

in the presence of an acid ion exchange resin catalyst; and then further reacting the compound having the structure:

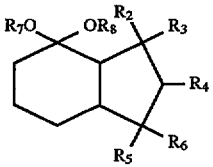

in the presence of an acid ion exchange catalyst in order to form the composition of matter defined according to the structure:

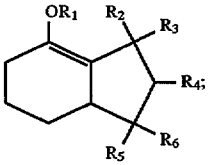

and then isolating the composition of matter defined according to the structure:

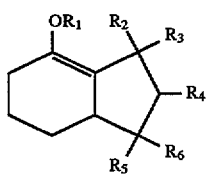

wherein $R_1$ is methyl or ethyl; wherein $R_4$ represents methyl or hydrogen; wherein $R_2$, $R_3$, $R_5$ and $R_6$ each represents methyl or ethyl with the provisos that:

(1) at least three of $R_2$, $R_3$, $R_5$ and $R_6$ represent methyl; and (2) when each of $R_2$, $R_3$, $R_5$ and $R_6$ is methyl, then $R_4$ is methyl wherein $R_7$ and $R_8$ are the same or different methyl or ethyl; and wherein $R_9$ is methyl or ethyl with the proviso that when $R_9$ is methyl, $R_7$ and $R_8$ are both methyl; and when $R_9$ is ethyl, $R_7$ and $R_8$ are both ethyl; and with the further proviso that when $R_1$ is methyl, $R_7$, $R_8$ and $R_9$ are methyl and when $R_1$ is ethyl, $R_7$, $R_8$ and $R_9$ are each ethyl.

* * * * *